US011073476B2

(12) United States Patent
Hu

(10) Patent No.: US 11,073,476 B2
(45) Date of Patent: Jul. 27, 2021

(54) METHOD FOR DEVELOPING BIOLOGICAL TRACE EVIDENCE ON POROUS OBJECT

(71) Applicant: SUZHOU XIAOSONG SCIENCE & TECHNOLOGY DEVELOPMENT CO., LTD, Jiangsu (CN)

(72) Inventor: Xiaosong Hu, Jiangsu (CN)

(73) Assignee: SUZHOU XIAOSONG SCIENCE & TECHNOLOGY DEVELOPMENT CO., LTD, Suzhou (CN)

(*) Notice: Subject to any disclaimer, the term of this patent is extended or adjusted under 35 U.S.C. 154(b) by 83 days.

(21) Appl. No.: 16/479,707

(22) PCT Filed: Aug. 9, 2017

(86) PCT No.: PCT/CN2017/096564
§ 371 (c)(1),
(2) Date: Jul. 22, 2019

(87) PCT Pub. No.: WO2018/133389
PCT Pub. Date: Jul. 26, 2018

(65) Prior Publication Data
US 2021/0010937 A1 Jan. 14, 2021

(30) Foreign Application Priority Data
Jan. 22, 2017 (CN) .......................... 201710045379.1

(51) Int. Cl.
G01N 21/64 (2006.01)
A61B 5/1172 (2016.01)
(52) U.S. Cl.
CPC ........ *G01N 21/6428* (2013.01); *A61B 5/1172* (2013.01); *G01N 2021/6439* (2013.01)
(58) Field of Classification Search
CPC .................. G01N 21/6428; G01N 2021/6439
See application file for complete search history.

(56) References Cited

U.S. PATENT DOCUMENTS

| 4,176,205 A | 11/1979 | Molina |
| 2009/0269478 A1 | 10/2009 | Nalewajek et al. |
| 2011/0076383 A1 | 3/2011 | Reedy et al. |

FOREIGN PATENT DOCUMENTS

| CN | 202104921 U | 1/2012 |
| CN | 102908149 A | 2/2013 |

(Continued)

OTHER PUBLICATIONS

Danna E. Bicknell, et al., "Use of an Optimized 1,2-Indanedione Process for the Development of Latent Prints", Sep. 2008, Journal of Forensic Sciences, vol. 53, No. 5, 1 (Sep. 1, 2008), pp. 1108-1116. (Year: 2008).*

(Continued)

*Primary Examiner* — Samuel P Siefke
*Assistant Examiner* — Henry H Nguyen
(74) *Attorney, Agent, or Firm* — Schmeiser, Olsen & Watts, LLP

(57) ABSTRACT

Provided is a method for developing biological trace evidence on a porous object, including immersing a porous object in a biological fluorescent development reagent or spraying the reagent on the porous object, drying the porous object in an environment having a relative humidity of less than 40% at a temperature of 50° C.-120° C. irradiating the dried porous object with a laser having a wavelength of 532 nm and a full width at half-maximum of less than 1 nm, controlling a surface of the porous object with an illuminance of over 300,000 lux, and using a cut-off filter under 540 nm to develop the biological trace evidence. A raw material formulation of the reagent is, in percent by weight, 0.02%-0.5% of indanedione, 4%-10% of ethyl acetate, 0.5%-1.5% of glycerol, 5%-15.5% of pure alcohol, and 73.5%-90% of petroleum ether.

18 Claims, 15 Drawing Sheets

(56) References Cited

FOREIGN PATENT DOCUMENTS

Figure 1:
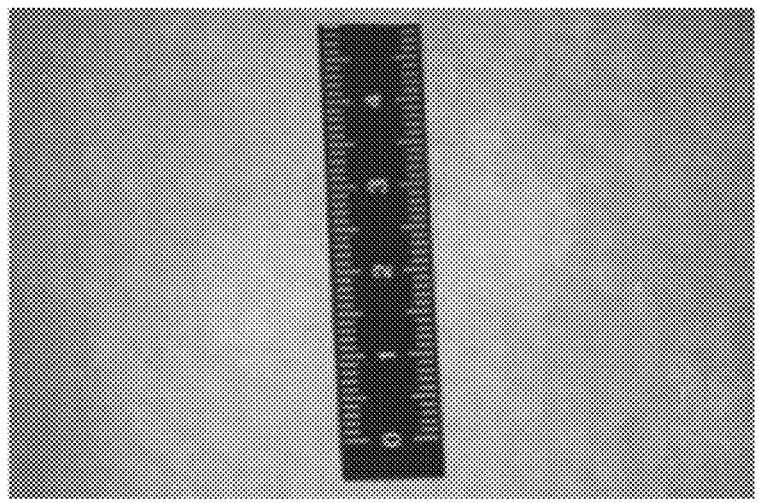

| CN | 104605860 | A  | 5/2015 |
|----|-----------|----|--------|
| CN | 105527258 | A  | 4/2016 |
| CN | 106802292 | A  | 6/2017 |
| CX | 105527258 | A  | 4/2016 |
| WO | 2009067761 | A1 | 6/2009 |
| WO | WO2009067761 | A1 | 6/2009 |

OTHER PUBLICATIONS

Translation of Xiaosong, Hu, CN 104605860 A, May 13, 2015 (Year: 2015).*
Translation of Wu, Shiyu, CN 102908149 A, Feb. 6, 2013 (Year: 2013).*
Bleay, S. M., et al., "Fingerprint Source Book", Feb. 2015, Home Office Centre for Applied Science and Technology (Year: 2015).*
International Search Report for PCT/CN2017/096564.
Zhoutao—Two Visualization Methods of Fingerprints on Porous Objects and Damp Non-porous Objects; China Public Security Academy Edition 2016 No. 4 Sum. No. 45.
Dutta—Fingerprint visualization enhancement by deposition of columnar thin films and fluorescent dye treatment; Forensic Science International 228 (2013).

* cited by examiner

METHOD FOR DEVELOPING BIOLOGICAL TRACE EVIDENCE ON POROUS OBJECT

CROSS-REFERENCE TO RELATED APPLICATIONS

This application claims priority to PCT Application No. PCT/CN2017/096564, having a filing date of Aug. 9, 2017, which is based on Chinese Application No. 201710045379.1, having a filing date of Jan. 22, 2017, the entire contents both of which are hereby incorporated by reference.

FIELD OF TECHNOLOGY

The following relates to a method for developing biological trace evidence on a porous object.

BACKGROUND

In the field of criminal evidence reconnaissance, it is necessary to discover and obtain criminal evidences left by suspects, including fingerprint evidence, palmprint evidence, and trace evidence that can reflect DNA characteristics, thereby constructing an evidence chain of criminal facts and laying a legal evidence basis for punishing crimes.

In the known art, there were reports on the use of indanedione for developing a handprint, and the inventor had also proposed a method for developing a handprint using indanedione in Chinese Patent CN201510093460.8, which uses indanedione, glacial acetic acid, ethyl acetate and petroleum ether as raw materials to prepare a fluorescent development reagent, and which can well extract a handprint on a brick, a wooden stick, a fabric and a leather. However, during use, it was found that the fluorescent development reagent used in the method has a strong irritating odor, which is easy to cause discomfort to the operator, and the storage period of the fluorescent development reagent is only 2 weeks, which also requires to be stored at 4° C. low temperature, the prepared fluorescent development reagent can only be used within 2 weeks, and when more than 2 weeks, the fluorescent development reagent may crystallize or produce other variations, and cannot be used, which is easy to cause waste. Further, when the fluorescent development reagent is sprayed, the phenomenon that the precipitated crystals block the nozzle is likely to occur, resulting in uneven spraying.

SUMMARY

An aspect relates to a method for developing biological trace evidence on a porous object, and a biological fluorescent development reagent used in this method produces no obvious acid odor, and thus does not cause any unpleasant experience to operator.

The present disclosure further provides a biological fluorescent development reagent.

To solve the above technical problems, the present disclosure employs the following technical solution:
a method for developing biological trace evidence on a porous object, comprises immersing a porous object in a biological fluorescent development reagent or spraying a biological fluorescent development reagent on the porous object, drying the porous object in an environment having a relative humidity of less than 40% at a temperature of 50° C.-120° C., irradiating the dried porous object with a laser having a wavelength of 532 nm and a full width at half-maximum of less than 1 nm, controlling a surface of the porous object with an illuminance of over 300,000 lux, and using a cut-off filter under 540 nm to develop biological trace evidence on the porous object, and a raw material formulation of the biological fluorescent development reagent is, in percent by weight, 0.02%-0.5% of indanedione, 4%-10% of ethyl acetate, 0.5%-1.5% of glycerol, 5%-15.5% of pure alcohol, and 73.5%-90% of petroleum ether.

In the present disclosure, the biological trace evidence comprises a handprint.

In some embodiments, the handprint refers to a fingerprint or a palmprint.

In the present disclosure, a cut-off filter at 540 nm refers to a cut-off filter that allows only light waves of or above 540 nm to pass through, while other light waves cannot pass.

The method of the present disclosure is applicable to various porous objects such as porous objects with high permeability, specifically including napkin, toilet paper, thermal paper, invoice paper, etc.; such as porous objects with moderate permeability, specifically including writing paper, cloth, etc.; such as porous objects with weak permeability, specifically including brick, wood, and stone.

For the porous objects with high permeability, a biological fluorescent development reagent with a relatively low mass concentration of indanedione can be used; for the porous objects with moderate permeability, a biological fluorescent development reagent with a moderate mass concentration of indanedione can be used; for the porous objects with weak permeability, a biological fluorescent development reagent with a relatively high mass concentration of indanedione can be used. However, if the concentration of indanedione is too high, the resulting handprint pattern is easily blurred and cannot be used, and when a low concentration of indanedione is used, a clear handprint pattern is easily generated, and if the concentration is too low, the handprint may also be unclear or cannot be seen.

In a specific implementation, when the porous object is a napkin, toilet paper, thermal paper or invoice paper, the raw material formulation of the biological fluorescent development reagent is, in percent by weight, 0.02%-0.15% of indanedione, 4%-10% of ethyl acetate, 0.5%-1.5% of glycerol, 5%-15.5% of pure alcohol, and 74%-90% of petroleum ether.

When the porous object is a writing paper or cloth, the raw material formulation of the biological fluorescent development reagent is, in percent by weight, 0.05%-0.25% of indanedione, 4%-10% of ethyl acetate, 0.5%-1.5% of glycerol, 5%-15.5% of pure alcohol, and 74%-90% of petroleum ether.

When the porous object is a brick, wood or stone, the raw material formulation of the biological fluorescent development reagent is, in percent by weight, 0.2%-0.5% of indanedione, 4%-10% of ethyl acetate, 0.5%-1.5% of glycerol, 5%-15.5% of pure alcohol, and 73.5%-89% of petroleum ether.

In the present disclosure, pure alcohol refers to >99.7% absolute ethanol, $C_2H_5OH$.

When immersing the porous object in the biological fluorescent development reagent, the immersing time is controlled to be 5-10 sec.

Before immersing in the biological fluorescent development reagent or spraying the biological fluorescent development reagent, a moisture content of the porous object is controlled to be less than 8%.

Before immersing in the biological fluorescent development reagent or spraying the biological fluorescent development reagent, the moisture content of the porous object is controlled to be 6-7%.

The porous object is dried in an environment having a relative humidity of less than 30% at a temperature of 50° C.-90° C.

A method for preparing the biological fluorescent development reagent comprises following steps:
(1) dissolving glycerin in pure alcohol to obtain a solution 1;
(2) dissolving indanedione in ethyl acetate to obtain a solution 2;
(3) mixing the solution 1 obtained in the step (1) and the solution 2 obtained in the step (2), adding petroleum ether, and uniformly stirring the mixture to give the biological fluorescent development reagent.

The present disclosure provides another technical solution:
A biological fluorescent development reagent for developing biological trace evidence on a porous object is provided, and a raw material formulation of the biological fluorescent development reagent is, in percent by weight, 0.02%-0.5% of indanedione, 4%-10% of ethyl acetate, 0.5%-1.5% of glycerol, 5%-15.5% of pure alcohol, and 73.5%-90% of petroleum ether.

The present disclosure further provides an alternative technical solution:
a method for developing biological trace evidence on a porous object comprises immersing a porous object in a biological fluorescent development reagent or spraying a biological fluorescent development reagent on the porous object, drying the porous object in an environment having a relative humidity of less than 40% at a temperature of 50° C.-120° C., irradiating the dried porous object with a laser having a wavelength of 532 nm and a full width at half-maximum of less than 1 nm, controlling a surface of the porous object with an illuminance of over 300,000 lux, and using a cut-off filter under 540 nm to develop the biological trace evidence on the porous object, a raw material formulation of the biological fluorescent development reagent is indanedione, ethyl acetate, glycerol, pure alcohol and petroleum ether; wherein, in volume ratio, ethyl acetate:glycerol:pure alcohol:petroleum ether=(3-8):(0.3-0.8):(5-15):(60-80); when preparing, indanedione is dissolved in ethyl acetate at a mass concentration of 0.0025-0.1 g/mL.

When the porous object is a napkin, toilet paper, thermal paper or invoice paper, the biological fluorescent development reagent is prepared by dissolving indanedione in ethyl acetate at a mass concentration of 0.0025-0.0333 g/mL. In a specific implementation, a preferable formulation of the biological fluorescent development reagent is, 0.02-0.10 g of indanedione; 3-8 mL of ethyl acetate, 0.3-0.8 mL of glycerol, 5-15 mL of pure alcohol, and 60-80 mL of petroleum ether.

When the porous object is a writing paper or cloth, the biological fluorescent development reagent is prepared by dissolving indanedione in ethyl acetate at a mass concentration of 0.00625-0.05 g/mL. In a specific implementation, a preferable formulation of the biological fluorescent development reagent is, 0.05-0.15 g of indanedione; 3-8 mL of ethyl acetate, 0.3-0.8 mL of glycerol, 5-15 mL of pure alcohol, and 60-80 mL of petroleum ether.

When the porous object is a brick, wood or stone, the biological fluorescent development reagent is prepared by dissolving indanedione in ethyl acetate at a mass concentration of 0.01875-0.1 g/mL. In a specific implementation, a preferable formulation of the biological fluorescent development reagent is, 0.15-0.30 g of indanedione; 3-8 mL of ethyl acetate, 0.3-0.8 mL of glycerol, 5-15 mL of pure alcohol, and 60-80 mL of petroleum ether.

The present disclosure further provides another alternative technical solution:

A biological fluorescent development reagent for developing biological trace evidence on a porous object, a raw material formulation of the biological fluorescent development reagent is indanedione, ethyl acetate, glycerol, pure alcohol and petroleum ether; wherein, in volume ratio, ethyl acetate:glycerol:pure alcohol:petroleum ether=(3-8):(0.3-0.8):(5-15):(60-80); when preparing, indanedione is dissolved in ethyl acetate at a mass concentration of 0.0025-0.1 g/mL.

Due to the implementation of the above technical solution, the present disclosure has the following advantages over the known art:

The biological fluorescent development reagent used in the present disclosure produces no obvious acid odor, and thus does not cause any unpleasant experience to operator.

Glycerol is used in the biological fluorescent development reagent used in the method of the present disclosure, and glycerol has a function of slow volatility, and therefore, when the spraying method is employed, the phenomenon that the precipitated crystals block the nozzle will not occur after spraying a plurality of times (four times or more).

The storage condition of the fluorescent development reagent of the present disclosure is widened, and the appearance of crystallization will not occur after storage at room temperature (25° C.) for 30 days.

BRIEF DESCRIPTION

Figure 2:
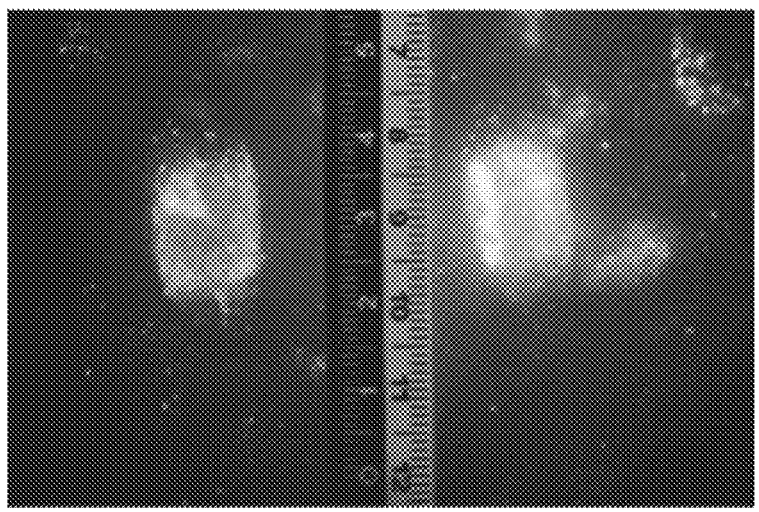
Figure 3:
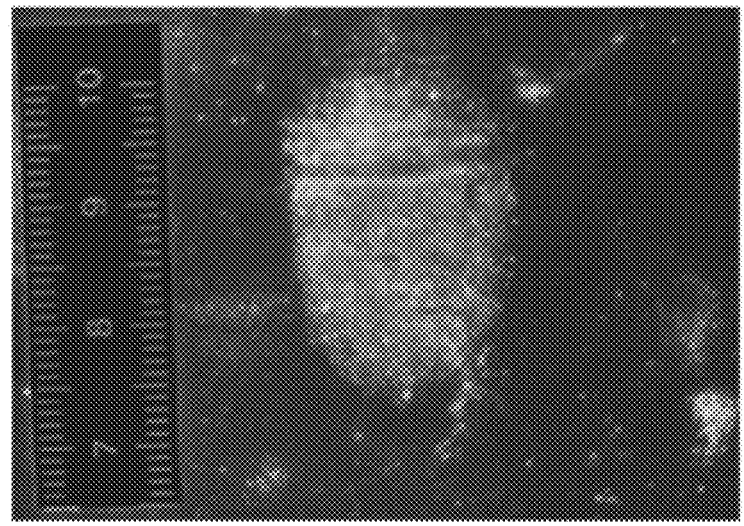
Figure 4:
Figure 5:
Figure 6:
Figure 7:
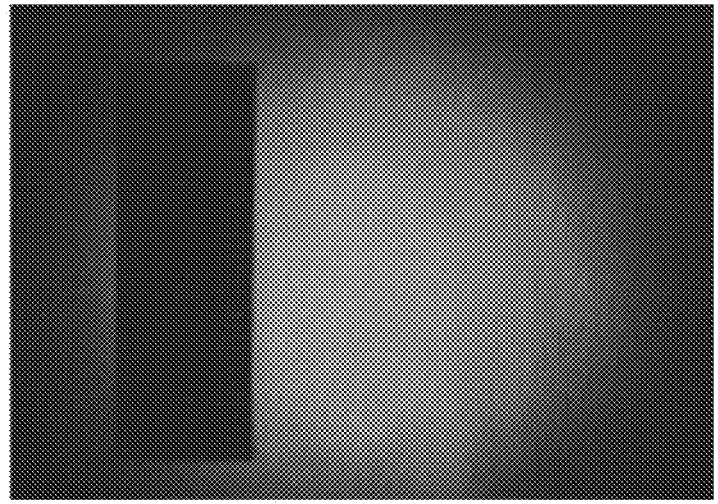
Figure 8:
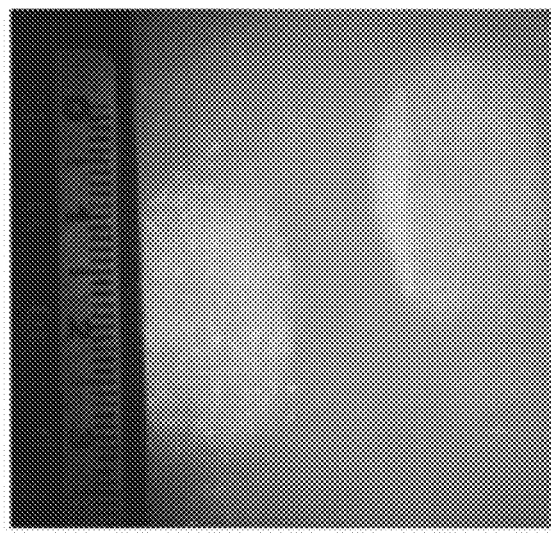
Figure 9:
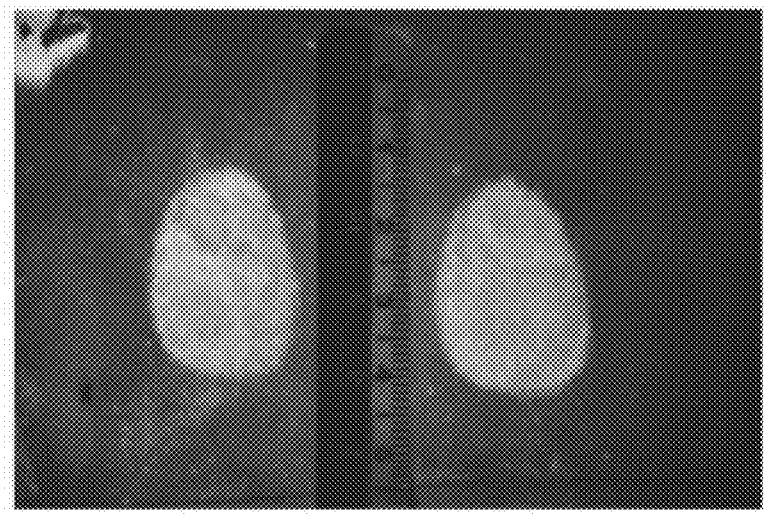
Figure 10:
Figure 11:
Figure 12:
Figure 13:
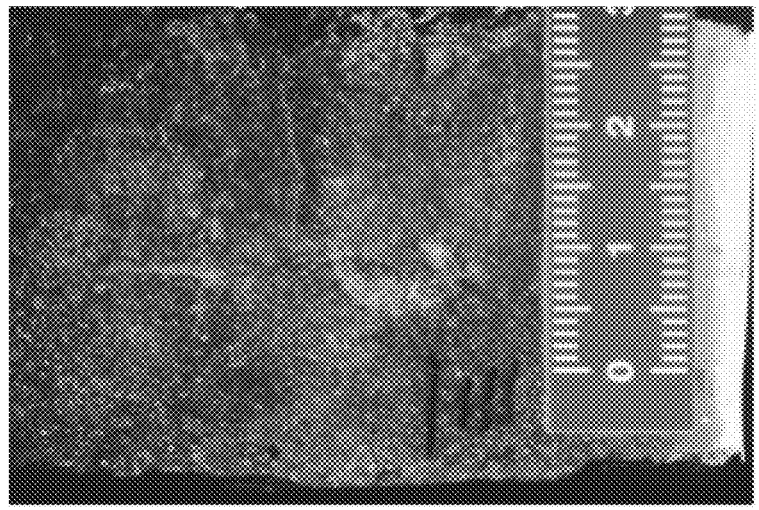
Figure 14:
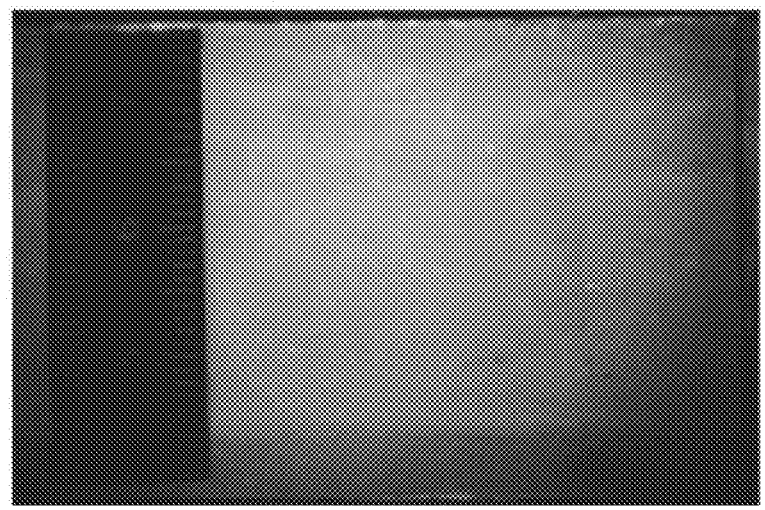
Figure 15:
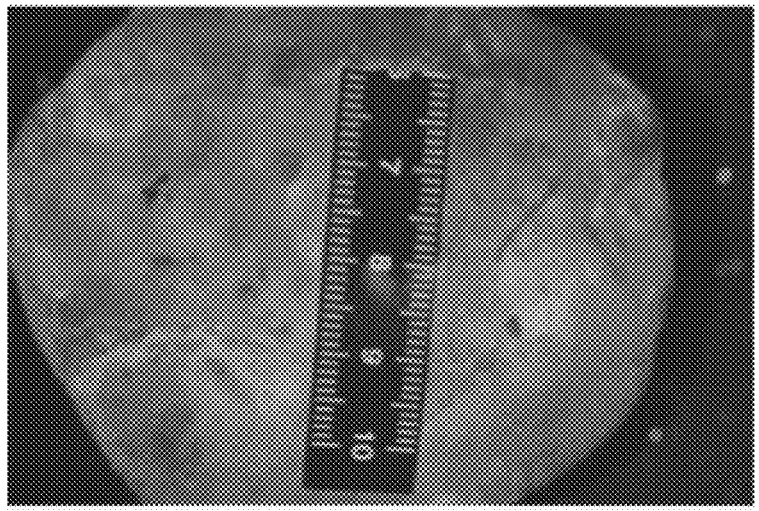
Figure 16:
Figure 17:
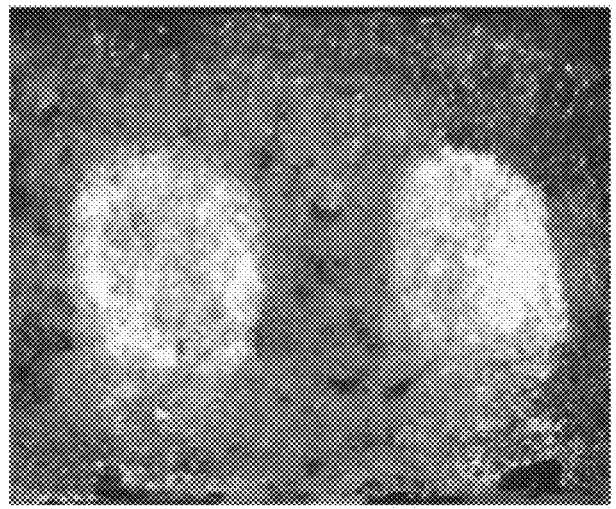
Figure 18:
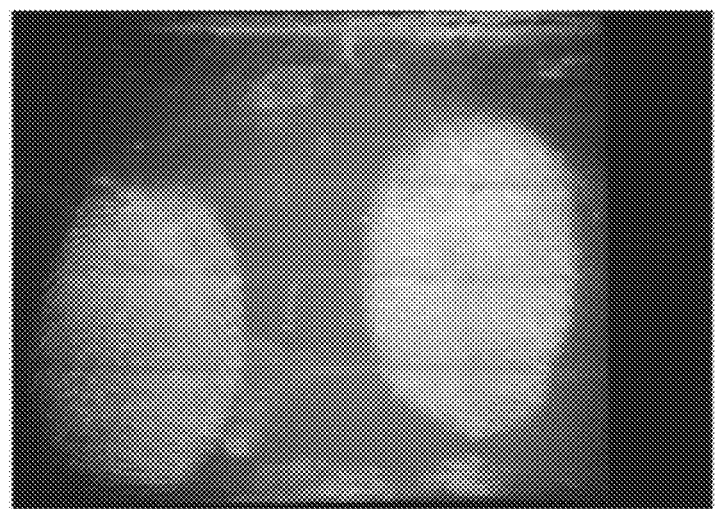
Figure 19:
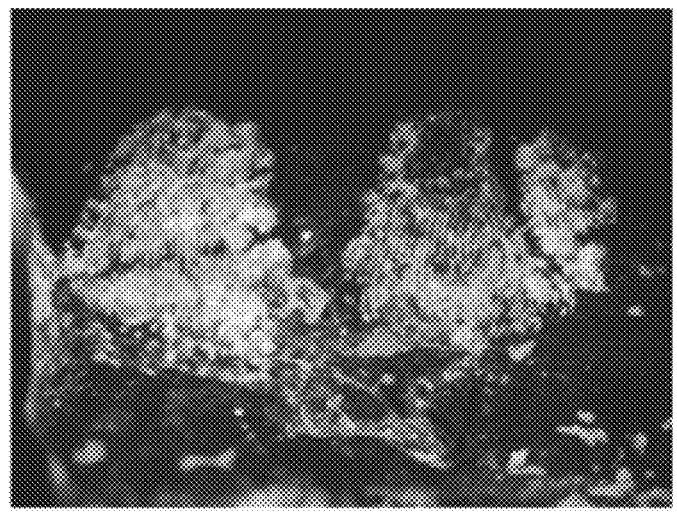
Figure 20:
Figure 21:
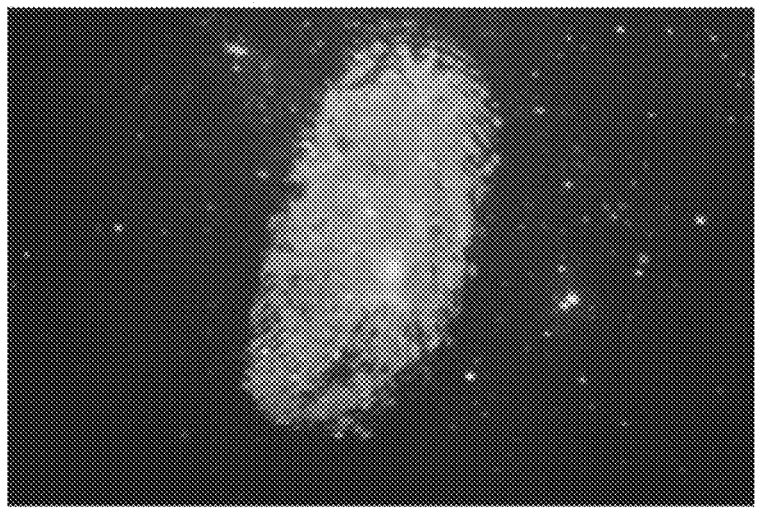
Figure 22:
Figure 23:
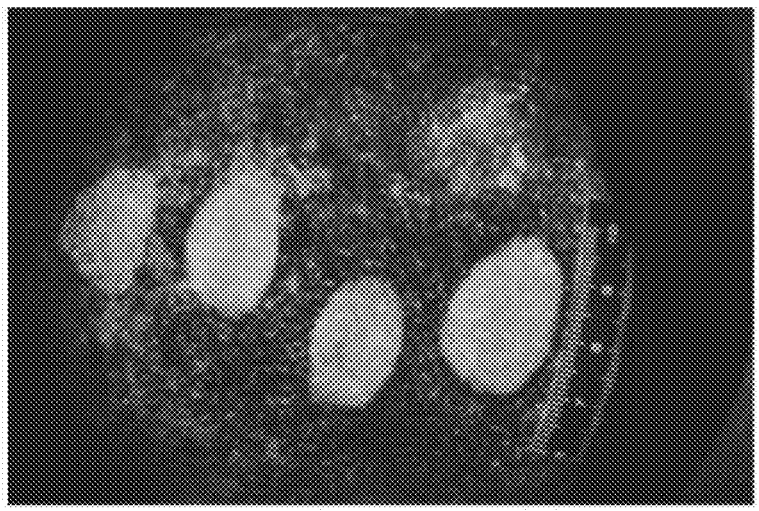
Figure 24:
Figure 25:
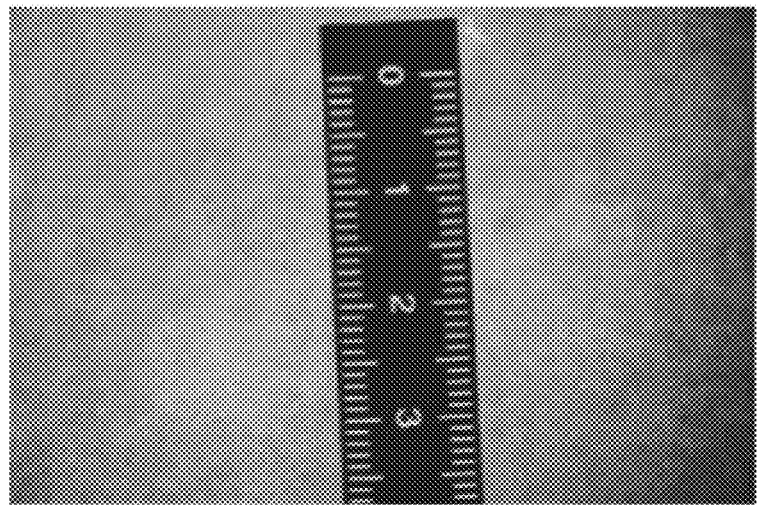
Figure 26:
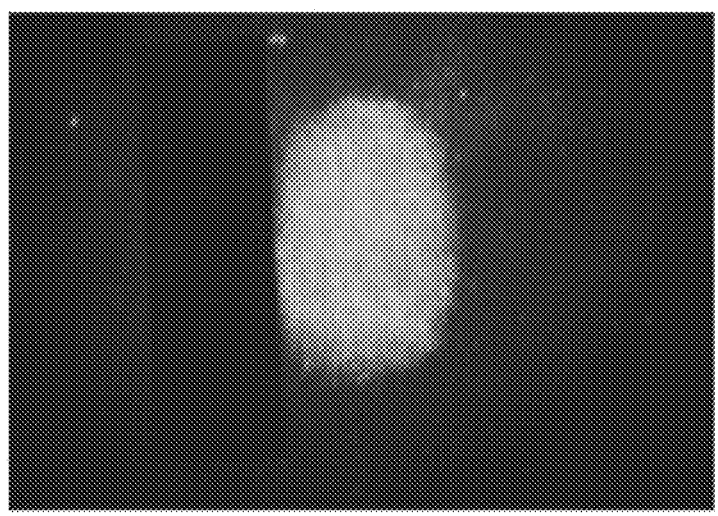
Figure 27:
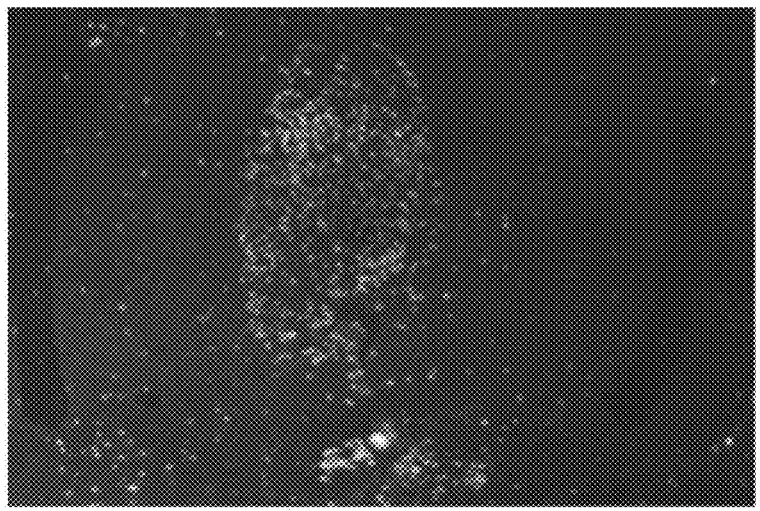
Figure 28:
Figure 29:
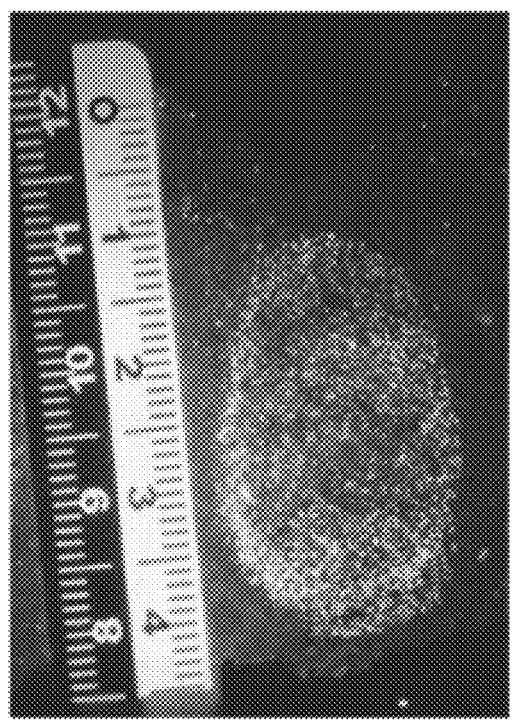

Some of the embodiments will be described in detail, with references to the following Figures, wherein like designations denote like members, wherein:

FIG. 1 is a photo of a fingerprint of Embodiment 1;
FIG. 2 is a photo of a fingerprint of Embodiment 2;
FIG. 3 is a photo of a fingerprint of Embodiment 3;
FIG. 4 is a state diagram of a reagent used in Embodiment 1 after being stored for 30 days;
FIG. 5 is a state diagram of a reagent used in Embodiment 2 after being stored for 30 days;
FIG. 6 is a state diagram of a reagent used in Embodiment 3 after being stored for 30 days;
FIG. 7 is a photo of a fingerprint of Embodiment 4;
FIG. 8 is a photo of a fingerprint of Embodiment 5;
FIG. 9 is a photo of a fingerprint of Embodiment 6;
FIG. 10 is a state diagram of a reagent used in Embodiment 4 after being stored for 30 days;
FIG. 11 is a state diagram of a reagent used in Embodiment 5 after being stored for 30 days;
FIG. 12 is a state diagram of a reagent used in Embodiment 6 after being stored for 30 days;
FIG. 13 is a photo of a fingerprint of Embodiment 7;
FIG. 14 is a photo of a fingerprint of Embodiment 8;
FIG. 15 is a photo of a fingerprint of Embodiment 9;
FIG. 16 is a state diagram of a reagent used in Embodiment 7 after being stored for 30 days;
FIG. 17 is a photo of a fingerprint of Embodiment 10;
FIG. 18 is a photo of a fingerprint of Embodiment 11;
FIG. 19 is a photo of a fingerprint of Embodiment 12;
FIG. 20 is a state diagram of a reagent used in Embodiment 10 after being stored for 30 days;
FIG. 21 is a photo of a fingerprint of Embodiment 13;
FIG. 22 is a photo of a fingerprint of Embodiment 14;
FIG. 23 is a photo of a fingerprint of Embodiment 15;

FIG. 24 is a state diagram of a reagent used in Embodiment 13 after being stored for 30 days;
FIG. 25 is a photo of a fingerprint of Control 1;
FIG. 26 is a photo of a fingerprint of Control 2;
FIG. 27 is a photo of a fingerprint of Control 3;
FIG. 28 is a photo of a fingerprint of Control 4; and
FIG. 29 is a photo of a fingerprint of Control 5.

DETAILED DESCRIPTION

In the following, the present disclosure is further explained in detail combining with the specific embodiments, but not limited to these embodiments.

Embodiment 1 (the Sample is a Napkin with a Fingerprint)

This embodiment provides a method for developing a handprint on a porous object, and a formulation of a biological fluorescent development reagent used in this method was: indanedione 0.02 g; ethyl acetate 3 mL; glycerol 0.3 mL; pure alcohol 5 mL; petroleum ether 75 mL.

The developing method comprises the following steps:
(1) The moisture content of the napkin was controlled by drying to be less than 7%.
(2) In an environment of 25° C. and a relative humidity of 60%, 0.3 mL glycerol was added into 5 mL pure alcohol, and the solution was thoroughly stirred and dissolved to prepare a solution 1; 0.02 g indanedione was sufficiently dissolved in 3 mL ethyl acetate to prepare a solution 2, and the mass concentration of indanedione was 0.0067 g/mL; the solution 1 and the solution 2 were mixed, then 75 mL petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The napkin was immersed in the biological fluorescent development reagent for 5 sec.
(4) After the attached reagent on the soaked napkin was volatilized under the ambient temperature (25° C.), the napkin was dried in an environment with a relative humidity of less than 30% and a temperature of 50° C.-55° C. for 10 min.
(5) The dried napkin was irradiated with a laser having a wavelength of 532 nm and a full width at half-maximum of less than 1 nm, an illuminance of 300,000 lux was controlled to be formed on a surface of the napkin, and the handprint was obtained by photographing under a 540 nm filter, see FIG. 1.

The state of the biological fluorescent development reagent used in the method of this embodiment after 30 days of storage is shown in FIG. 4, and it was found that there was no crystallization or other variation appeared in the reagent.

Embodiment 2 (the Sample is a Napkin with a Fingerprint)

This embodiment provides a method for developing a handprint on a porous object, and a formulation of a biological fluorescent development reagent used in this method was: indanedione 0.05 g; ethyl acetate 5 mL; glycerol 0.5 mL; pure alcohol 10 mL; petroleum ether 75 mL.

The developing method comprises the following steps:
(1) The moisture content of the napkin was controlled by drying to be less than 7%.
(2) In an environment of 25° C. and a relative humidity of 60%, 0.5 mL glycerol was added into 10 mL pure alcohol, and the solution was thoroughly stirred and dissolved to prepare a solution 1; 0.05 g indanedione was sufficiently dissolved in 5 mL ethyl acetate to prepare a solution 2, and the mass concentration of indanedione was 0.01 g/mL; the solution 1 and the solution 2 were mixed, then 75 mL petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The napkin was immersed in the fluorescent development reagent for 5 sec.
(4) After the attached reagent on the soaked napkin was volatilized under the ambient temperature (25° C.), the napkin was dried in an environment with a relative humidity of less than 30% and a temperature of 50° C.-55° C. for 10 min.
(5) The dried napkin was irradiated with a laser having a wavelength of 532 nm and a full width at half-maximum of less than 1 nm, an illuminance of 300,000 lux was controlled to be formed on a surface of the napkin, and the handprint was obtained by photographing under a 540 nm filter, see FIG. 2.

The state of the biological fluorescent development reagent used in the method of this embodiment after 30 days of storage is shown in FIG. 5, and it was found there was no crystallization or other variation appeared in the reagent.

Embodiment 3 (the Sample is a Napkin with a Fingerprint)

This embodiment provides a method for developing a handprint on a porous object, and a formulation of a biological fluorescent development reagent used in this method was: indanedione 0.10 g; ethyl acetate 8 mL; glycerol 0.8 mL; pure alcohol 15 mL; petroleum ether 75 mL.

The developing method comprises the following steps:
(1) The moisture content of the napkin was controlled by drying to be less than 7%.
(2) In an environment of 25° C. and a relative humidity of 60%, 0.8 mL glycerol was added into 15 mL pure alcohol, and the solution was thoroughly stirred and dissolved to prepare a solution 1; 0.10 g indanedione was sufficiently dissolved in 8 mL ethyl acetate to prepare a solution 2, and the mass concentration of indanedione was 0.0125 g/mL; the solution 1 and the solution 2 were mixed, then 75 mL petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The napkin was immersed in the fluorescent development reagent for 5 sec.
(4) After the attached reagent on the soaked napkin was volatilized under the ambient temperature (25° C.), the napkin was dried in an environment with a relative humidity of less than 30% and a temperature of 50° C.-55° C. for 10 min.
(5) The dried napkin was irradiated with a laser having a wavelength of 532 nm and a full width at half-maximum of less than 1 nm, an illuminance of 300,000 lux was controlled to be formed on a surface of the napkin, and the handprint was obtained by photographing under a 540 nm filter, see FIG. 3.

The state of the biological fluorescent development reagent used in the method of this embodiment after 30 days of storage is shown in FIG. 6, and it was found that there was no crystallization or other variation appeared in the reagent.

Embodiment 4 (the Sample is a Cotton Cloth with a Fingerprint)

This embodiment provides a method for developing a handprint on a porous object, and a formulation of a biological fluorescent development reagent used in this method was: indanedione 0.05 g; ethyl acetate 3 mL; glycerol 0.3 mL; pure alcohol 5 mL; petroleum ether 75 mL.

The developing method comprises the following steps:
(1) The moisture content of the cotton cloth was controlled by drying to be less than 7%.
(2) In an environment of 25° C. and a relative humidity of 60%, 0.3 mL glycerol was added into 5 mL pure alcohol, and the solution was thoroughly stirred and dissolved to prepare a solution 1; 0.05 g indanedione was sufficiently dissolved in 3 mL ethyl acetate to prepare a solution 2, and the mass concentration of indanedione was 0.0167 g/mL; the solution 1 and the solution 2 were mixed, then 75 mL of petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The cotton cloth was immersed in the fluorescent development reagent for 8 sec.
(4) After the attached reagent on the soaked cotton cloth was volatilized under the ambient temperature (25° C.), the cotton cloth was dried in an environment with a relative humidity of less than 30% and a temperature of 60° C.-65° C. for 10 min.
(5) The dried cotton cloth was irradiated with a laser having a wavelength of 532 nm and a full width at half-maximum of less than 1 nm, an illuminance of 300,000 lux was controlled to be formed on a surface of the cotton cloth, and the handprint was obtained by photographing under a 540 nm filter, see FIG. 7.

The state of the biological fluorescent development reagent used in the method of this embodiment after 30 days of storage is shown in FIG. 10, and it was found that there was no crystallization or other variation appeared in the reagent.

Embodiment 5 (the Sample is a Cotton Cloth with a Fingerprint)

This embodiment provides a method for developing a handprint on a porous object, and a formulation of a biological fluorescent development reagent used in this method was: indanedione 0.10 g; ethyl acetate 5 mL; glycerol 0.5 mL; pure alcohol 10 mL; petroleum ether 75 mL.

The developing method comprises the following steps:
(1) The moisture content of the cotton cloth was controlled by drying to be less than 7%.
(2) In an environment of 25° C. and a relative humidity of 60%, 0.5 mL glycerol was added into 10 mL pure alcohol, and the solution was thoroughly stirred and dissolved to prepare a solution 1; 0.10 g indanedione was sufficiently dissolved in 5 mL ethyl acetate to prepare a solution 2, and the mass concentration of indanedione was 0.02 g/mL; the solution 1 and the solution 2 were mixed, then 75 mL petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The cotton cloth was immersed in the fluorescent development reagent for 8 sec.
(4) After the attached reagent on the soaked cotton cloth was volatilized under the ambient temperature (25° C.), the cotton cloth was dried in an environment with a relative humidity of less than 30% and a temperature of 60° C.-65° C. for 10 min.
(5) The dried cotton cloth was irradiated with a laser having a wavelength of 532 nm and a full width at half-maximum of less than 1 nm, an illuminance of 300,000 lux was controlled to be formed on a surface of the cotton cloth, and the handprint was obtained by photographing under a 540 nm filter, see FIG. 8.

The state of the biological fluorescent development reagent used in the method of this embodiment after 30 days of storage is shown in FIG. 11, and it was found that there was no crystallization or other variation appeared in the reagent.

Embodiment 6 (the Sample is a Cotton Cloth with a Fingerprint)

This embodiment provides a method for developing a handprint on a porous object, and a formulation of a biological fluorescent development reagent used in this method was: indanedione 0.15 g; ethyl acetate 8 mL; glycerol 0.8 mL; pure alcohol 15 mL; petroleum ether 75 mL.

The developing method comprises the following steps:
(1) The moisture content of the cotton cloth was controlled by drying to be less than 7%.
(2) In an environment of 25° C. and a relative humidity of 60%, 0.8 mL of glycerol was added into 15 mL pure alcohol, and the solution was thoroughly stirred and dissolved to prepare a solution 1; 0.15 g indanedione was sufficiently dissolved in 8 mL ethyl acetate to prepare a solution 2, and the mass concentration of indanedione was 0.01875 g/mL; the solution 1 and the solution 2 were mixed, then 75 mL petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The cotton cloth was immersed in the fluorescent development reagent for 8 sec.
(4) After the attached reagent on the soaked cotton cloth was volatilized under the ambient temperature (25° C.), the cotton cloth was dried in an environment with a relative humidity of less than 30% and a temperature of 60° C.-65° C. for 10 min.
(5) The dried cotton cloth was irradiated with a laser having a wavelength of 532 nm and a full width at half-maximum of less than 1 nm, an illuminance of 300,000 lux was controlled to be formed on a surface of the cotton cloth, and the handprint was obtained by photographing under a 540 nm filter, see FIG. 9.

The state of the biological fluorescent development reagent used in the method of this embodiment after 30 days of storage is shown in FIG. 12, and it was found that there was no crystallization or other variation appeared in the reagent.

Embodiment 7 (the Sample is a Brick with a Fingerprint)

This embodiment provides a method for developing a handprint on a porous object, and a formulation of a biological fluorescent development reagent used in this method was: indanedione 0.15 g; ethyl acetate 3 mL; glycerol 0.3 mL; pure alcohol 5 mL; petroleum ether 75 mL.

The developing method comprises the following steps:
(1) The moisture content of the brick was controlled by drying to be less than 7%.
(2) In an environment of 25° C. and a relative humidity of 60%, 0.3 mL glycerol was added into 5 mL pure alcohol, and the solution was thoroughly stirred and dissolved to prepare a solution 1; 0.15 g indanedione was sufficiently dissolved in 3 mL ethyl acetate to prepare a solution 2, and the mass concentration of indanedione was 0.05 g/mL; the solution 1 and the solution 2 were mixed, then 75 mL petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The brick was immersed in the fluorescent development reagent for 10 sec.
(4) After the attached reagent on the soaked brick was volatilized under the ambient temperature (25° C.), the brick was dried in an environment with a relative humidity of less than 30% and a temperature of 80° C.-85° C. for 12 min.
(5) The dried brick was irradiated with a laser having a wavelength of 532 nm and a full width at half-maximum of less than 1 nm, an illuminance of 500,000 lux was controlled to be formed on a surface of the brick, and the handprint was obtained by photographing under a 540 nm filter, see FIG. 13.

The state of the biological fluorescent development reagent used in the method of this embodiment after 30 days of storage is shown in FIG. 16, and it was found that there was no crystallization or other variation appeared in the reagent.

Embodiment 8 (the Sample is a Wood with a Fingerprint)

This embodiment provides a method for developing a handprint on a porous object, and the biological fluorescent development reagent used in this embodiment was the same with that used in Embodiment 7.

The developing method comprises the following steps:
(1) The moisture content of the wood was controlled by drying to be less than 7%.
(2) In an environment of 25° C. and a relative humidity of 60%, 0.3 mL glycerol was added into 5 mL pure alcohol, and the solution was thoroughly stirred and dissolved to prepare a solution 1; 0.15 g indanedione was sufficiently dissolved in 3 mL ethyl acetate to prepare a solution 2, and the mass concentration of indanedione was 0.05 g/mL; the solution 1 and the solution 2 were mixed, then 75 mL of petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The wood was immersed in the fluorescent development reagent for 10 sec.
(4) After the attached reagent on the soaked wood was volatilized under the ambient temperature (25° C.), the wood was dried in an environment with a relative humidity of less than 30% and a temperature of 70° C.-75° C. for 12 min.
(5) The dried wood was irradiated with a laser having a wavelength of 532 nm and a full width at half-maximum of less than 1 nm, an illuminance of 500,000 lux was controlled to be formed on a surface of the wood, and the handprint was obtained by photographing under a 540 nm filter, see FIG. 14.

Embodiment 9 (the Sample is a Stone with a Fingerprint)

This embodiment provides a method for developing a handprint on a porous object, and the biological fluorescent development reagent used in this embodiment was the same with that used in Embodiment 7.

The developing method comprises the following steps:
(1) The moisture content of the stone was controlled by drying to be less than 7%.
(2) In an environment of 25° C. and a relative humidity of 60%, 0.3 mL glycerol was added into 5 mL pure alcohol, and the solution was thoroughly stirred and dissolved to prepare a solution 1; 0.15 g indanedione was sufficiently dissolved in 3 mL ethyl acetate to prepare a solution 2, and the mass concentration of indanedione was 0.05 g/mL; the solution 1 and the solution 2 were mixed, then 75 mL petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The stone was immersed in the fluorescent development reagent for 10 sec.
(4) After the attached reagent on the soaked stone was volatilized under the ambient temperature (25° C.), the stone was dried in an environment with a relative humidity of less than 30% and a temperature of 80° C.-85° C. for 15 min.
(5) The dried stone was irradiated with a laser having a wavelength of 532 nm and a full width at half-maximum of less than 1 nm, an illuminance of 500,000 lux was controlled to be formed on a surface of the stone, and the handprint was obtained by photographing under a 540 nm filter, see FIG. 15.

Embodiment 10 (the Sample is a Brick with a Fingerprint)

This embodiment provides a method for developing a handprint on a porous object, and a formulation of a biological fluorescent development reagent used in this method was: indanedione 0.20 g; ethyl acetate 5 mL; glycerol 0.5 mL; pure alcohol 10 mL; petroleum ether 75 mL.

The developing method comprises the following steps:
(1) The moisture content of the brick was controlled by drying to be less than 7%.
(2) In an environment of 25° C. and a relative humidity of 60%, 0.5 mL glycerol was added into 10 mL pure alcohol, and the solution was thoroughly stirred and dissolved to prepare a solution 1; 0.20 g indanedione was sufficiently dissolved in 5 mL ethyl acetate to prepare a solution 2, and the mass concentration of indanedione was 0.04 g/mL; the solution 1 and the solution 2 were mixed, then 75 mL petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The brick was immersed in the fluorescent development reagent for 10 sec.
(4) After the attached reagent on the soaked brick was volatilized under the ambient temperature (25° C.), and then dried in an environment with a relative humidity of less than 30% and a temperature of 80° C.-85° C. for 12 min.
(5) The dried brick was irradiated with a laser having a wavelength of 532 nm and a full width at half-maximum of less than 1 nm, an illuminance of 500,000 lux was controlled to be formed on a surface of the brick, and the handprint was obtained by photographing under a 540 nm filter, see FIG. 17.

The state of the biological fluorescent development reagent used in the method of this embodiment after 30 days of storage is shown in FIG. 20, and it was found that there was no crystallization or other variation appeared in the reagent.

Embodiment 11 (the Sample is a Wood with a Fingerprint)

This embodiment provides a method for developing a handprint on a porous object, and the biological fluorescent development reagent used in this embodiment was the same with that used in Embodiment 10.
The developing method comprises the following steps:
(1) The moisture content of the wood was controlled by drying to be less than 7%.
(2) In an environment of 25° C. and a relative humidity of 60%, 0.5 mL glycerol was added into 10 mL pure alcohol, and the solution was thoroughly stirred and dissolved to prepare a solution 1; 0.20 g indanedione was sufficiently dissolved in 5 mL of ethyl acetate to prepare a solution 2, and the mass concentration of indanedione was 0.04 g/mL; the solution 1 and the solution 2 were mixed, then 75 mL petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The wood was immersed in the fluorescent development reagent for 10 sec.
(4) After the attached reagent on the soaked wood was volatilized under the ambient temperature (25° C.), the wood was dried in an environment with a relative humidity of less than 30% and a temperature of 70° C.-75° C. for 12 min.
(5) The dried wood was irradiated with a laser having a wavelength of 532 nm and a full width at half-maximum of less than 1 nm, an illuminance of 500,000 lux was controlled to be formed on a surface of the wood, and the handprint was obtained by photographing under a 540 nm filter, see FIG. 18.

Embodiment 12 (the Sample is a Stone with a Fingerprint)

This embodiment provides a method for developing a handprint on a porous object, and the biological fluorescent development reagent used in this embodiment was the same with that used in Embodiment 10.
The developing method comprises the following steps:
(1) The moisture content of the stone was controlled by drying to be less than 7%.
(2) In an environment of 25° C. and a relative humidity of 60%, 0.5 mL glycerol was added into 10 mL pure alcohol, and the solution was thoroughly stirred and dissolved to prepare a solution 1; 0.20 g indanedione was sufficiently dissolved in 5 mL ethyl acetate to prepare a solution 2, and the mass concentration of indanedione was 0.04 g/mL; the solution 1 and the solution 2 were mixed, then 75 mL petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The stone was immersed in the fluorescent development reagent for 10 sec.
(4) After the attached reagent on the soaked stone was volatilized under the ambient temperature (25° C.), and then dried in an environment with a relative humidity of less than 30% and a temperature of 80° C.-85° C. for 15 min.
(5) The dried stone was irradiated with a laser having a wavelength of 532 nm and a full width at half-maximum of less than 1 nm, an illuminance of 500,000 lux was controlled to be formed on a surface of the stone, and the handprint was obtained by photographing under a 540 nm filter, see FIG. 19.

Embodiment 13 (the Sample is a Brick with a Fingerprint)

This embodiment provides a method for developing a handprint on a porous object, and a formulation of a biological fluorescent development reagent used in this method was: indanedione 0.30 g; ethyl acetate 8 mL; glycerol 0.8 mL; pure alcohol 15 mL; petroleum ether 75 mL.
The developing method comprises the following steps:
(1) The moisture content of the brick was controlled by drying to be less than 7%.
(2) In an environment of 25° C. and a relative humidity of 60%, 0.8 mL glycerol was added into 15 mL pure alcohol, and the solution was thoroughly stirred and dissolved to prepare a solution 1; 0.30 g indanedione was sufficiently dissolved in 8 mL ethyl acetate to prepare a solution 2, and the mass concentration of indanedione was 0.0375 g/mL; the solution 1 and the solution 2 were mixed, then 75 mL petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The brick was immersed in the fluorescent development reagent for 10 sec.
(4) After the attached reagent on the soaked brick was volatilized under the ambient temperature (25° C.), and then dried in an environment with a relative humidity of less than 30% and a temperature of 80° C.-85° C. for 12 min.
(5) The dried brick was irradiated with a laser having a wavelength of 532 nm and a full width at half-maximum of less than 1 nm, an illuminance of 500,000 lux was controlled to be formed on a surface of the brick, and the handprint was obtained by photographing under a 540 nm filter, see FIG. 21.

The state of the biological fluorescent development reagent used in the method of this embodiment after 30 days of storage is shown in FIG. 24, and it was found that was no crystallization or other variation appeared in the reagent.

Embodiment 14 (the Sample is a Wood with a Fingerprint)

This embodiment provides a method for developing a handprint on a porous object, and the biological fluorescent development reagent used in this embodiment was the same with that used in Embodiment 13.

The developing method comprises the following steps:
(1) The moisture content of the wood was controlled by drying to be less than 7%.
(2) In an environment of 25° C. and a relative humidity of 60%, 0.8 mL glycerol wad added into 15 mL pure alcohol, and the solution was thoroughly stirred and dissolved to prepare a solution 1; 0.30 g indanedione was sufficiently dissolved in 8 mL ethyl acetate to prepare a solution 2, and the mass concentration of indanedione was 0.0375 g/mL; the solution 1 and the solution 2 were mixed, then 75 mL petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The wood was immersed in the fluorescent development reagent for 10 sec.
(4) After the attached reagent on the soaked wood was volatilized under the ambient temperature (25° C.), the wood was dried in an environment with a relative humidity of less than 30% and a temperature of 70° C.-75° C. for 12 min.
(5) The dried wood was irradiated with a laser having a wavelength of 532 nm and a full width at half-maximum of less than 1 nm, an illuminance of 500,000 lux was controlled to be formed on a surface of the wood, and the handprint was obtained by photographing under a 540 nm filter, see FIG. 22.

Embodiment 15 (the Sample is a Stone with a Fingerprint)

This embodiment provides a method for developing a handprint on a porous object, and the biological fluorescent development reagent used in this embodiment was the same with that used in Embodiment 13.

The developing method comprises the following steps:
(1) The moisture content of the stone was controlled by drying to be less than 7%.
(2) In an environment of 25° C. and a relative humidity of 60%, 0.8 mL glycerol was added into 15 mL pure alcohol, and the solution was thoroughly stirred and dissolved to prepare a solution 1; 0.30 g indanedione was sufficiently dissolved in 8 mL ethyl acetate to prepare a solution 2, and the mass concentration of indanedione was 0.0375 g/mL; the solution 1 and the solution 2 were mixed, then 75 mL petroleum ether was added, stirred and dissolved, and formulated into a biological fluorescent development reagent, and the biological fluorescent development reagent was used after it was ready, and if storage was required, it was stored in a brown light-proof bottle at normal temperature 25° C. or below 25° C. and used up within 30 days.
(3) The stone was immersed in the fluorescent development reagent for 10 sec.
(4) After the attached reagent on the soaked stone was volatilized under the ambient temperature (25° C.), the stone was dried in an environment with a relative humidity of less than 30% and a temperature of 80° C.-85° C. for 15 min.
(5) The dried stone was irradiated with a laser having a wavelength of 532 nm and a full width at half-maximum of less than 1 nm, an illuminance of 500,000 lux was controlled to be formed on a surface of the stone, and the handprint was obtained by photographing under a 540 nm filter, see FIG. 23.

Control 1 (the Sample is a Napkin with a Fingerprint)

This control embodiment provides a method for developing a handprint on a porous object, and a formulation of a biological fluorescent development reagent used in this method was: indanedione 0.01 g; ethyl acetate 2 mL; glycerol 0.2 mL; pure alcohol 4 mL; petroleum ether 75 mL.

The developing method comprises the following steps:
(1) The moisture content of the napkin was controlled by drying to be less than 7%.
(2) In an environment of 25° C. and a relative humidity of 60%, 0.2 mL glycerol was added into 4 mL pure alcohol, and the solution was thoroughly stirred and dissolved to prepare a solution 1; 0.01 g indanedione was sufficiently dissolved in 2 mL ethyl acetate to prepare a solution 2; the solution 1 and the solution 2 were mixed, then 75 mL petroleum ether was added, stirred and dissolved, and formulated into a fluorescent development reagent, and the fluorescent development reagent was used after it was ready, and if storage was required, it was stored in a brown light-proof bottle at normal temperature 25° C. or below 25° C. and used up within 30 days.
(3) The napkin was immersed in the fluorescent development reagent for 5 sec.
(4) After the attached reagent on the soaked napkin was volatilized under the ambient temperature (25° C.), the napkin was dried in an environment with a relative humidity of less than 30% and a temperature of 50° C.-55° C. for 10 min.
(5) The dried napkin was irradiated with a laser having a wavelength of 532 nm and a full width at half-maximum of less than 1 nm, an illuminance of 300,000 lux was controlled to be formed on a surface of the napkin, and the handprint was obtained by photographing under a 540 nm filter, see FIG. 25.

Control 2 (the Sample is a Cotton Cloth with a Fingerprint)

This control embodiment provides a method for developing a handprint on a porous object, and a formulation of a biological fluorescent development reagent used in this method was: indanedione 0.20 g; ethyl acetate 10 mL; glycerol 1.0 mL; pure alcohol 15 mL; petroleum ether 75 mL.

The developing method comprises the following steps:
(1) The moisture content of the cotton cloth was controlled by drying to be less than 7%.
(2) In an environment of 25° C. and a relative humidity of 60%, 1.0 mL of glycerol was added into 15 mL pure alcohol, and the solution was thoroughly stirred and dissolved to prepare a solution 1; 0.20 g indanedione was sufficiently dissolved in 10 mL ethyl acetate to prepare a solution 2; the solution 1 and the solution 2 were mixed, then 75 mL petroleum ether was added, stirred and dissolved, and formulated into a fluorescent development reagent, and the fluorescent development reagent was used after it was ready, and if storage was required, it was stored in a brown light-proof bottle at normal temperature 25° C. or below 25° C. and used up within 30 days.

(3) The cotton cloth was immersed in the fluorescent development reagent for 8 sec.
(4) After the attached reagent on the soaked cotton cloth was volatilized under the ambient temperature (25° C.), the cotton cloth was dried in an environment with a relative humidity of less than 30% and a temperature of 60° C.-65° C. for 10 min.
(5) The dried cotton cloth was irradiated with a laser having a wavelength of 532 nm and a full width at half-maximum of less than 1 nm, an illuminance of 300,000 lux was controlled to be formed on a surface of the cotton cloth, and the handprint was obtained by photographing under a 540 nm filter, see FIG. 26.

Control 3 (the Sample is a Brick with a Fingerprint)

This control embodiment provides a method for developing a handprint on a porous object, and a formulation of a biological fluorescent development reagent used in this method was: indanedione 0.10 g; ethyl acetate 2 mL; glycerol 0.2 mL; pure alcohol 4 mL; petroleum ether 75 mL.

The developing method comprises the following steps:
(1) The moisture content of the brick was controlled by drying to be less than 7%.
(2) In an environment of 25° C. and a relative humidity of 60%, 0.2 mL glycerol was added into 4 mL pure alcohol, and the solution was thoroughly stirred and dissolved to prepare a solution 1; 0.10 g indanedione was sufficiently dissolved in 2 mL ethyl acetate to prepare a solution 2; the solution 1 and the solution 2 were mixed, then 75 mL petroleum ether was added, stirred and dissolved, and formulated into a fluorescent development reagent, and the fluorescent development reagent was used after it was ready, and if storage was required, it was stored in a brown light-proof bottle at normal temperature 25° C. or below 25° C. and used up within 30 days.
(3) The brick was immersed in the fluorescent development reagent for 10 sec.
(4) After the attached reagent on the soaked brick was volatilized under the ambient temperature (25° C.), the brick was dried in an environment with a relative humidity of less than 30% and a temperature of 80° C.-85° C. for 12 min.
(5) The dried brick was irradiated with a laser having a wavelength of 532 nm and a full width at half-maximum of less than 1 nm, an illuminance of 500,000 lux was controlled to be formed on a surface of the brick, and the handprint was obtained by photographing under a 540 nm filter, see FIG. 27.

Control 4 (the Sample is a Wood with a Fingerprint)

This control embodiment provides a method for developing a handprint on a porous object, and the biological fluorescent development reagent used in this control embodiment was the same with that used in Control 3.

The developing method comprises the following steps:
(1) The moisture content of the wood was controlled by drying to be less than 7%.
(2) In an environment of 25° C. and a relative humidity of 60%, 0.2 mL glycerol was added into 4 mL pure alcohol, and the solution was thoroughly stirred and dissolved to prepare a solution 1; 0.10 g indanedione was sufficiently dissolved in 2 mL ethyl acetate to prepare a solution 2; the solution 1 and the solution 2 were mixed, then 75 mL petroleum ether was added, stirred and dissolved, and formulated into a fluorescent development reagent, and the fluorescent development reagent was used after it was ready, and if storage was required, it was stored in a brown light-proof bottle at normal temperature 25° C. or below 25° C. and used up within 30 days.
(3) The wood was immersed in the fluorescent development reagent for 10 sec.
(4) After the attached reagent on the soaked wood was volatilized under the ambient temperature (25° C.), the wood was dried in an environment with a relative humidity of less than 30% and a temperature of 70° C.-75° C. for 12 min.
(5) The dried wood was irradiated with a laser having a wavelength of 532 nm and a full width at half-maximum of less than 1 nm, an illuminance of 500,000 lux was controlled to be formed on a surface of the wood, and the handprint was obtained by photographing under a 540 nm filter, see FIG. 28.

Control 5 (the Sample is a Stone with a Fingerprint)

This control embodiment provides a method for developing a handprint on a porous object, and the biological fluorescent development reagent used in this control embodiment was the same with that used in Control 3.

The developing method comprises the following steps:
(1) The moisture content of the stone was controlled by drying to be less than 7%.
(2) In an environment of 25° C. and a relative humidity of 60%, 0.2 mL glycerol was added into 4 mL pure alcohol, and the solution was thoroughly stirred and dissolved to prepare a solution 1; 0.10 g indanedione was sufficiently dissolved in 2 mL ethyl acetate to prepare a solution 2; the solution 1 and the solution 2 were mixed, then 75 mL petroleum ether was added, stirred and dissolved, and formulated into a fluorescent development reagent, and the fluorescent development reagent was used after it was ready, and if storage was required, it was stored in a brown light-proof bottle at normal temperature 25° C. or below 25° C. and used up within 30 days.
(3) The stone was immersed in the fluorescent development reagent for 10 sec.
(4) After the attached reagent on the soaked stone was volatilized under the ambient temperature (25° C.), the stone was dried in an environment with a relative humidity of less than 30% and a temperature of 80° C.-85° C. for 15 min.
(5) The dried stone was irradiated with a laser having a wavelength of 532 nm and a full width at half-maximum of less than 1 nm, an illuminance of 500,000 lux was controlled to be formed on a surface of the stone, and the handprint was obtained by photographing under a 540 nm filter, see FIG. 29.

The biological fluorescent development reagent used in the present disclosure is very suitable for spraying, so after it is sprayed on the sample, the solvent can be volatilized very quickly, and the handprint can be quickly developed, which is very suitable for the requirement of rapid development.

The above detailed describes the present disclosure, is intended to make those skilled in the art being able to understand the present disclosure and thereby implement it, and should not be concluded to limit the protective scope of this disclosure. Any equivalent variations or modifications according to the essence of the present disclosure should be covered by the protective scope of the present disclosure.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

What is claimed is:

1. A method for developing biological trace evidence on a porous object, comprising:
   immersing the porous object in a biological fluorescent development reagent or spraying the biological fluorescent development reagent on the porous object;
   drying the porous object in an environment having a relative humidity of less than 40% at a temperature of 50° C.-120° C.;
   irradiating the dried porous object with a laser having a wavelength of 532 nm and a full width at half-maximum of less than 1 nm;
   controlling a surface of the porous object with an illuminance of over 300,000 lux; and
   using a cut-off filter at 540 nm to develop the biological trace evidence on the porous object;
   wherein a raw material formulation of the biological fluorescent development reagent is, in percent by weight, 0.02%-0.5% of indanedione, 4%-10% of ethyl acetate, 0.5%-1.5% of glycerol, 5%-15.5% of pure alcohol, and 73.5%-90% of petroleum ether.

2. The method according to claim 1, wherein the porous object comprises a napkin, toilet paper, thermal paper, invoice paper, writing paper, cloth, brick, wood, or stone.

3. The method according to claim 1, wherein the porous object is a napkin, toilet paper, thermal paper or invoice paper, the raw material formulation of the biological fluorescent development reagent is, in percent by weight, 0.02%-0.15% of indanedione, 4%-10% of ethyl acetate, 0.5%-1.5% of glycerol, 5%-15.5% of pure alcohol, and 74%-90% of petroleum ether.

4. The method according to claim 1, wherein the porous object is a writing paper or cloth, the raw material formulation of the biological fluorescent development reagent is, in percent by weight, 0.05%-0.25% of indanedione, 4%-10% of ethyl acetate, 0.5%-1.5% of glycerol, 5%-15.5% of pure alcohol, and 74%-90% of petroleum ether.

5. The method according to claim 1, wherein the porous object is a brick, wood or stone, the raw material formulation of the biological fluorescent development reagent is, in percent by weight, 0.2%-0.5% of indanedione, 4%-10% of ethyl acetate, 0.5%-1.5% of glycerol, 5%-15.5% of pure alcohol, and 73.5%-89% of petroleum ether.

6. The method according to claim 1, wherein, before immersing in the biological fluorescent development reagent or spraying the biological fluorescent development reagent, a moisture content of the porous object is controlled to be less than 8%.

7. The method according to claim 1, wherein the porous object is dried in the environment having a relative humidity of less than 30% at a temperature of 50° C.-90° C.

8. The method according to claim 1, wherein the biological trace evidence comprises a handprint.

9. The method according to claim 1, wherein, a method for preparing the biological fluorescent development reagent comprises:
   (1) dissolving glycerin in pure alcohol to obtain a first solution;
   (2) dissolving indanedione in ethyl acetate to obtain a second solution; and
   (3) mixing the first solution obtained in the step (1) and the second solution obtained in the step (2), adding petroleum ether, and stirring to give the biological fluorescent development reagent.

10. A method for developing biological trace evidence on a porous object, comprising:
    immersing the porous object in a biological fluorescent development reagent or spraying the biological fluorescent development reagent on the porous object;
    drying the porous object in an environment having a relative humidity of less than 40% at a temperature of 50° C.-120° C.;
    irradiating the dried porous object with a laser having a wavelength of 532 nm and a full width at half-maximum of less than 1 nm;
    controlling a surface of the porous object with an illuminance of over 300,000 lux; and
    using a cut-off filter at 540 nm to develop the biological trace evidence on the porous object;
    wherein a raw material formulation of the biological fluorescent development reagent is indanedione, ethyl acetate, glycerol, pure alcohol and petroleum ether;
    wherein, in volume ratio, ethyl acetate:glycerol:pure alcohol:petroleum ether=(3-8):(0.3-0.8):(5-15):(60-80);
    when preparing, indanedione is dissolved in ethyl acetate at a mass concentration of 0.0025-0.1 g/mL.

11. The method according to claim 10, wherein the porous object comprises a napkin, toilet paper, thermal paper, invoice paper, writing paper, cloth, brick, wood, or stone.

12. The method according to claim 10, wherein the porous object is a napkin, toilet paper, thermal paper or invoice paper, the biological fluorescent development reagent is prepared by dissolving indanedione in ethyl acetate at a mass concentration of 0.0025-0.0333 g/mL.

13. The method according to claim 10, wherein the porous object is a writing paper or cloth, the biological fluorescent development reagent is prepared by dissolving indanedione in ethyl acetate at a mass concentration of 0.00625-0.05 g/mL.

14. The method according to claim 10, wherein the porous object is a brick, wood or stone, the biological fluorescent development reagent is prepared by dissolving indanedione in ethyl acetate at a mass concentration of 0.01875-0.1 g/mL.

15. The method according to claim 10, wherein, before immersing in the biological fluorescent development reagent or spraying the biological fluorescent development reagent, a moisture content of the porous object is controlled to be less than 8%.

16. The method according to claim 10, wherein the porous object is dried in the environment having a relative humidity of less than 30% at a temperature of 50° C.-90° C.

17. The method according to claim 10, wherein the biological trace evidence comprises a handprint.

18. The method according to claim 10, wherein, a method for preparing the biological fluorescent development reagent comprises:
    (1) dissolving glycerin in pure alcohol to obtain a first solution;
    (2) dissolving indanedione in ethyl acetate to obtain a second solution; and
    (3) mixing the first solution obtained in the step (1) and the second solution obtained in the step (2), adding petroleum ether, and stirring to give the biological fluorescent development reagent.

\* \* \* \* \*